(12) United States Patent
Batchelor et al.

(10) Patent No.: US 9,439,716 B2
(45) Date of Patent: Sep. 13, 2016

(54) BIPOLAR COAGULATION PROBE AND SNARE

(71) Applicant: GYRUS ACMI, INC., Southborough, MA (US)

(72) Inventors: Kester Batchelor, Mound, MN (US); Tracey Dobbs, Delano, MN (US); Jyue Boon Lim, New Brighton, MN (US); Nikhil Murdeshwar, Maple Grove, MN (US); Tsuyoshi Hayashida, Maple Grove, MN (US); Richard Curtis, Maple Grove, MN (US)

(73) Assignee: GYRUS ACMI, INC., Southborough, MA (US)

( * ) Notice: Subject to any disclaimer, the term of this patent is extended or adjusted under 35 U.S.C. 154(b) by 342 days.

(21) Appl. No.: 14/042,992

(22) Filed: Oct. 1, 2013

(65) Prior Publication Data

US 2015/0094719 A1 Apr. 2, 2015

(51) Int. Cl.
*A61B 18/14* (2006.01)
*A61B 17/221* (2006.01)
*A61B 18/00* (2006.01)
*A61B 18/12* (2006.01)

(52) U.S. Cl.
CPC ............ *A61B 18/14* (2013.01); *A61B 17/221* (2013.01); *A61B 18/1485* (2013.01); *A61B 2017/2212* (2013.01); *A61B 2018/00494* (2013.01); *A61B 2018/00559* (2013.01); *A61B 2018/00589* (2013.01); *A61B 2018/00595* (2013.01); *A61B 2018/00601* (2013.01); *A61B 2018/00916* (2013.01); *A61B 2018/00958* (2013.01); *A61B 2018/126* (2013.01); *A61B 2018/141* (2013.01); *A61B 2018/1467* (2013.01)

(58) Field of Classification Search
CPC .................. A61B 17/32056; A61B 2018/141; A61B 2017/00358
See application file for complete search history.

(56) References Cited

U.S. PATENT DOCUMENTS

| 4,493,320 A | 1/1985 | Treat |
| 4,532,924 A | 8/1985 | Auth et al. |
| 4,903,696 A * | 2/1990 | Stasz .................. A61B 18/1206 606/37 |

(Continued)

FOREIGN PATENT DOCUMENTS

| EP | 0997108 A2 | 5/2000 |
| WO | 2008/005411 A2 | 1/2008 |

OTHER PUBLICATIONS

Dec. 15, 2014 Search Report and Written Opinion issued in International Application No. PCT/US2014/055832.

*Primary Examiner* — Jocelyn D Ram
(74) *Attorney, Agent, or Firm* — Oliff PLC

(57) ABSTRACT

An electrosurgical device that can be used to remove pedunculated tissue structures such as polyps and certain uterine fibroids includes bipolar surface electrodes and a bipolar snare. The device includes a probe having a proximal end and a distal end, bipolar surface electrodes adjacent to the distal end of the probe, and a bipolar snare extending distally from the distal end of the probe and including first and second snare electrodes. The bipolar surface electrodes are separated from each other by a gap and extend over a portion of the distal end of the probe. Providing both a bipolar snare and bipolar surface electrodes advantageously reduces thermal spread from occurring (compared to the use of a monopolar snare) when using the snare to excise the tissue. The bipolar surface electrodes can be used to coagulate the point of excision.

10 Claims, 3 Drawing Sheets

(56) References Cited

U.S. PATENT DOCUMENTS

| | | | |
|---|---|---|---|
| 4,905,691 A | 3/1990 | Rydell | |
| 5,158,561 A * | 10/1992 | Rydell et al. | 606/113 |
| 5,282,799 A | 2/1994 | Rydell | |
| 5,336,222 A * | 8/1994 | Durgin, Jr. | A61B 18/1477 604/21 |
| 5,843,019 A * | 12/1998 | Eggers et al. | 604/22 |
| 5,919,189 A * | 7/1999 | Benderev | 606/45 |
| 6,050,995 A * | 4/2000 | Durgin | 606/47 |
| 6,110,169 A * | 8/2000 | Mueller et al. | 606/48 |
| 6,221,039 B1 * | 4/2001 | Durgin et al. | 604/22 |
| 6,610,056 B2 | 8/2003 | Durgin et al. | |
| 6,808,525 B2 * | 10/2004 | Latterell | A61B 18/1442 606/42 |
| 2003/0023237 A1 * | 1/2003 | Mollenauer | 606/27 |
| 2007/0208339 A1 * | 9/2007 | Arts et al. | 606/47 |
| 2014/0276798 A1 * | 9/2014 | Batchelor et al. | 606/42 |
| 2015/0126998 A1 * | 5/2015 | Batchelor et al. | 606/42 |

\* cited by examiner

BIPOLAR COAGULATION PROBE AND SNARE

BACKGROUND

This disclosure relates to systems for removing tissue from patients, and is particularly useful for removing pedunculated tissue structures such as polyps and pedunculated uterine fibroids.

Uterine fibroids are the most common pelvic tumor in women, affecting approximately one quarter of women during their reproductive years. Uterine fibroids are generally noncancerous, but may potentially lead to infertility or cause adverse effects if they occur during pregnancy. Typical symptoms include abnormal bleeding, pressure, or pain.

Uterine fibroids are categorized based on location on the uterus. Sub-mucosal fibroids form on the inside wall of the uterus; sub-serosal fibroids form on the outside wall of the uterus; intra-mural fibroids form within the wall of the uterus; and pedunculated fibroids are connected to the inside or outside wall of the uterus by a stalk.

Current uterine fibroid treatments include both pharmaceutical and surgical techniques. Pharmaceutical treatments often do not adequately treat the symptoms of uterine fibroids, ultimately necessitating surgical intervention. Surgical techniques include hysterectomy, myomectomy, endometrial ablation, myolysis and uterine artery occlusion. In addition, interventional radiology and high frequency focused ultrasound techniques exist for the treatment of uterine fibroids.

All of these treatment techniques suffer from shortcomings, such as the risk of relapse, infertility, and applicability to only one or a few types of uterine fibroids.

SUMMARY

The disclosed electrosurgical device, which is suited for removing pedunculated tissue structures such as, for example, polyps and certain fibroids, includes bipolar surface electrodes and a bipolar snare. In preferred embodiments, the device includes a probe having a proximal end and a distal end, bipolar surface electrodes adjacent to the distal end of the probe, and a bipolar snare extending distally from the distal end of the probe and including first and second snare electrodes. The bipolar surface electrodes are separated from each other by a gap and extend over a portion of the distal end of the probe.

Providing both a bipolar snare and bipolar surface electrodes advantageously reduces thermal spread from occurring (compared to the use of a monopolar snare) when using the snare to excise the pedunculated tissue structure. The bipolar surface electrodes can be used to coagulate the point of excision. Thus, the device is effective at minimizing bleeding. Further, by providing the snare and the coagulating surface electrodes on the same device, the procedure time is shortened.

The bipolar snare preferably includes an electrically insulative member disposed between distal ends of the first and second snare electrodes. In addition, an insulative material preferably is disposed between the bipolar surface electrodes.

The bipolar snare also includes a handpiece coupled to a proximal end of at least one of the snare electrodes. The handpiece can be manipulated by a user to tighten the bipolar snare around a part of a stem of a pedunculated tissue structure to be removed.

According to preferred embodiments, the bipolar surface electrodes include a first surface electrode and a second surface electrode separated from the first surface electrode by a gap. As noted above, the gap can include an insulative material to prevent short-circuiting from occurring between the first and second surface electrodes. Accordingly, when supplied with an appropriate signal, current will flow from the first surface electrode, through adjacent tissue, to the second surface electrode so as to coagulate the point of tissue excision. The first and second surface electrodes can be strips of electrically conductive material arranged so as to alternate with each other over the distal end of the probe. According to one embodiment, the first and second surface electrodes are formed into a double helix around the distal end of the probe.

The electrosurgical device also preferably includes first and second terminals by which the device is coupled to a bipolar energy source. In addition, the device includes circuitry coupling the first and second terminals to the bipolar surface electrodes and to the first and second snare electrodes. Such circuitry is used to control the supply of bipolar energy to the surface electrodes and to the snare electrodes. In preferred embodiments, the circuitry couples the first and second terminals to proximal ends of the bipolar surface electrodes and to proximal ends of the first and second snare electrodes.

According to some embodiments, the circuitry selectively causes one or the other of the snare electrodes and the surface electrodes to become "active." In such embodiments, the circuitry includes a switching device by which the first and second terminals are selectively coupled to either (i) the proximal ends of the bipolar surface electrodes, or (ii) the proximal ends of the first and second snare electrodes. According to some embodiments, the switching device includes (a) a first relay that selectively couples the first terminal to the proximal end of either a first one of the bipolar surface electrodes or the first snare electrode, and (b) a second relay that selectively couples the second terminal to the proximal end of either a second one of the bipolar surface electrodes or the second snare electrode.

According to one example, when in a first state, the first relay couples the first terminal to the proximal end of the first one of the bipolar surface electrodes while the second relay couples the second terminal to the proximal end of the second one of the bipolar surface electrodes. In addition, when in a second state, the first relay couples the first terminal to the proximal end of the first snare electrode while the second relay couples the second terminal to the proximal end of the second snare electrode.

According to another example, the first terminal is coupled to both the proximal end of a first one of the bipolar surface electrodes and to the proximal end of the first snare electrode, and the switching device includes a relay that selectively couples the second terminal to the proximal end of either a second one of the bipolar surface electrodes or the second snare electrode. For example, when in a first state, the relay couples the second terminal to the proximal end of the second bipolar surface electrode, and when in a second state, the relay couples the second terminal to the proximal end of the second snare electrode.

According to other embodiments, the circuitry can cause both the snare electrodes and the surface electrodes to be "active" at the same time. In such embodiments, the circuitry simultaneously couples (a) the first terminal to the proximal end of a first one of the bipolar surface electrodes and to the proximal end of the first snare electrode, and (b) the second terminal to the proximal end of a second one of the bipolar surface electrodes and to the proximal end of the second snare electrode. Accordingly, the bipolar surface electrodes and the bipolar snare electrodes can be concurrently supplied with power so that coagulation can be promoted as the pedunculated tissue structure is excised by the snare electrodes.

BRIEF DESCRIPTION OF THE DRAWINGS

Exemplary embodiments will be described in detail with reference to the following drawings in which.

DETAILED DESCRIPTION OF THE EMBODIMENTS

The following exemplary embodiments are described below with reference to the figures in the context of uterine fibroid treatment, and in particular removal of pedunculated uterine fibroids. However, the disclosed electrosurgical device is not limited to use for removing pedunculated fibroids. The device is suitable for removing various pedunculated tissue structures such as, for example, polyps located, for example, in the gastro-intestinal tract. Thus, although the following description is primarily focused on the removal of pedunculated uterine fibroids, other pedunculated tissue structures can be removed with the disclosed device.

Figure 1:
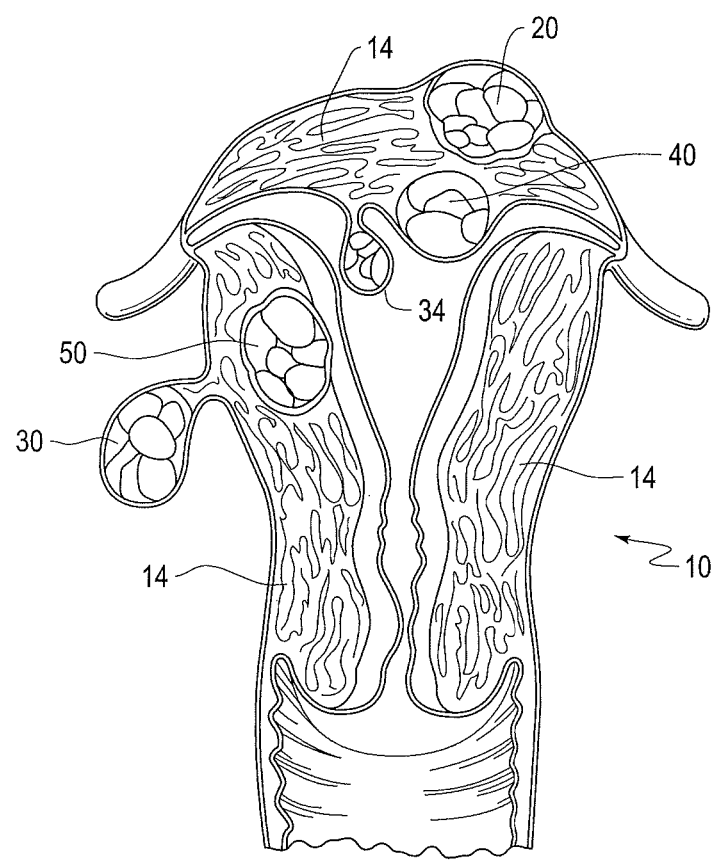
FIG. 1 illustrates various locations of uterine fibroids.

FIG. 1 illustrates different anatomical locations of uterine fibroids that can potentially afflict a patient. A sub-mucosal fibroid 40 is located on the inside wall of the uterus 10. A sub-serosal fibroid 20 is located on the outside wall of the uterus 10. An intra-mural fibroid 50 is located within the wall 14 of the uterus 10. A pedunculated fibroid 30 is attached to the outer wall of the uterus 10. Because it is attached to the outer wall of the uterus 10, fibroid 30 more specifically is known as a pedunculated sub-serosal fibroid. Fibroid 34 is known as a pedunculated sub-mucosal fibroid because it is attached to the inner wall of the uterus 10.

The location of a patient's fibroid(s) is first determined by one or more known imaging techniques. For example, ultrasonic imaging (known as "ultrasound") can be performed using a transducer placed externally of the patient's body or located within the uterus, for example, at the end of a transcervically inserted ultrasonic probe. MRI also could be used. Such technologies also can be used to locate polyps.

Once the location of the (or each) fibroid has been determined, the surgeon will determine how to access the fibroid(s). For example, pedunculated sub-mucosal fibroids typically are accessed transcervically, whereas pedunculated sub-serosal fibroids typically are accessed from the pelvic cavity (i.e., laproscopically accessed). However, the manner of accessing each fibroid also depends on the desired outcome of the surgery (e.g., fertility, resolution of the patient's symptoms, etc.), the size of each fibroid, as well as the location of other fibroids within the uterus.

Once the electrosurgical device has been inserted into the patient, the patient's uterus is manipulated into position to present the fibroid for treatment. The snare of the device then is looped around the fibroid and tightened to occlude the stalk of the pedunculated fibroid. The snare then is electrically activated to excise the fibroid. Bleeding at the point of excision is minimized by coagulation achieved with the bipolar surface electrodes provided at the distal end of the device. As will be described below, the surface electrodes can be activated concurrently with activation of the snare electrodes or after the snare electrodes have been activated. The excised fibroid then is extracted from the patient.

Figure 2:
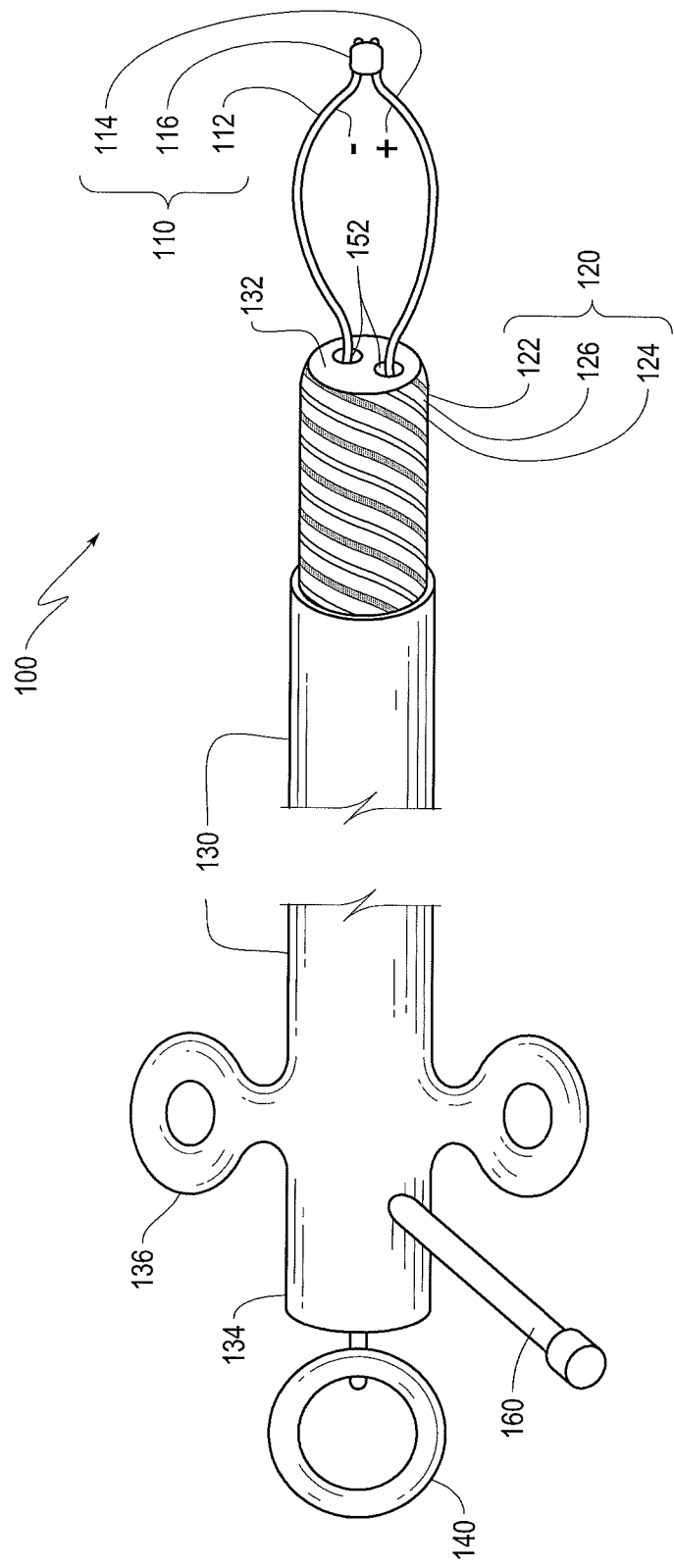
FIG. 2 is a side view of an electrosurgical device (a pedunculated tissue structure removal device) according to one embodiment of the invention.

An electrosurgical device (pedunculated tissue structure removal device) 100 according to one embodiment of the invention is shown in FIG. 2. The device 100 includes a probe (or probe body) 130 having a distal end 132, for insertion into the patient, and a proximal end 134 having a handle section 136 that is grasped by the surgeon. A bipolar snare 110 extends from apertures 152 in the distal end 132 of the probe 130. In addition, bipolar surface electrodes 120 are provided adjacent to the distal end 132 of the probe 130.

The bipolar snare 110 includes a first snare electrode 112 and a second snare electrode 114. Distal ends the first and second snare electrodes 112, 114 are attached to each other by an electrically insulative member 116 so that current does not flow between the distal ends of the electrodes 112, 114. Rather, when looped and tightened around the stalk of a pedunculated fibroid, and activated, current will flow from electrode 112 through the stalk and to electrode 114. The supplied current will be sufficient to cut through the stalk and detach the fibroid, which then can be removed by a grasper device such as forceps. A proximal end of at least one of the electrodes 112, 114 is attached to a pulling member 140 that can be moved by the surgeon so as to open or close the snare 110. FIG. 2 shows the snare in the open position. Once the snare has been located around the stalk of a pedunculated fibroid (or polyp), the surgeon moves the pulling member 140 proximally so as to tighten the snare 110 around the fibroid (or polyp) stalk.

Snares having pulling members are known, for example, from U.S. Pat. No. 4,493,320, U.S. Pat. No. 4,905,691 and U.S. Pat. No. 6,610,056, the disclosures of which are incorporated herein by reference in their entireties. Of these patents, U.S. Pat. No. 4,493,320 and U.S. Pat. No. 4,905,691 show bipolar snares, whereas U.S. Pat. No. 6,610,056 shows a monopolar snare.

The bipolar surface electrodes 120 include at least two different electrodes that are electrically isolated from each other. In the FIG. 2 embodiment, the bipolar surface electrodes include a first electrode 122 and a second electrode 124. An electrically insulative material 126 is provided in a gap between the first and second surface electrodes 122, 124. Accordingly, when supplied with an appropriate signal, current will flow from the first surface electrode 122, through adjacent tissue that contacts the first and second surface electrodes 122, 124, and then flow into the second surface electrode 124 so as to coagulate the point of fibroid (or polyp) excision. Although not shown in FIG. 2, proximal ends of the surface electrodes 122, 124 are attached to electrical conductors that extend through the probe 130 to contacts provided in an electrical connector 160 disposed near the proximal end 134 of the probe 130.

In the FIG. 2 embodiment, the first and second surface electrodes 122, 124 each are strips of electrically conductive material. In the FIG. 2 embodiment, the surface electrodes 122 and 124, spaced from each other, are spirally wound around a portion of the distal end 132 of the probe 130 to form a double helix. However, the surface electrodes can be arranged in ways other than a double helix. For example, the electrodes could extend longitudinally along the longitudinal axis of the distal portion 132 of the probe 130. As another alternative, the electrodes could be conductive pads that cover adjacent areas of the distal portion 132 of probe 130. See, for example, the aforementioned U.S. Pat. No. 6,610,056 and U.S. Pat. No. 4,532,924, the disclosures of which are incorporated herein by reference in their entireties.

Figure 3:
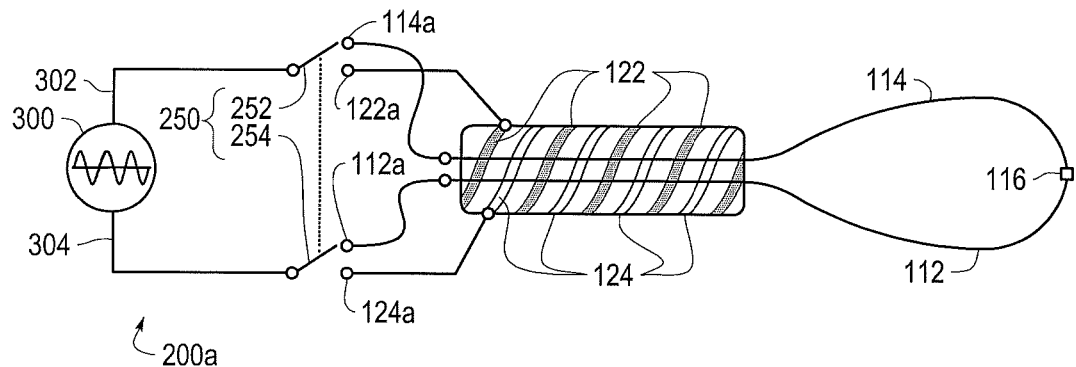
FIG. 3 is a diagram of circuitry that includes a first switching device by which the snare electrodes and the surface electrodes are selectively activated.
Figure 4:
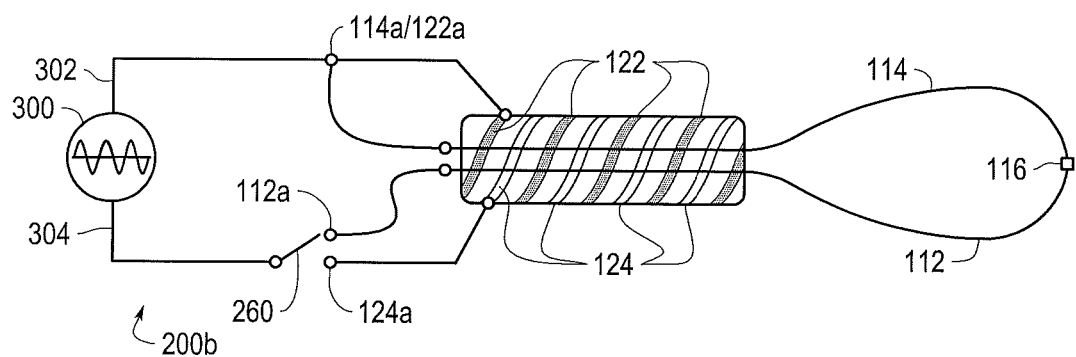
FIG. 4 is a diagram of circuitry that includes a second switching device by which the snare electrodes and the surface electrodes are selectively activated.
Figure 5:
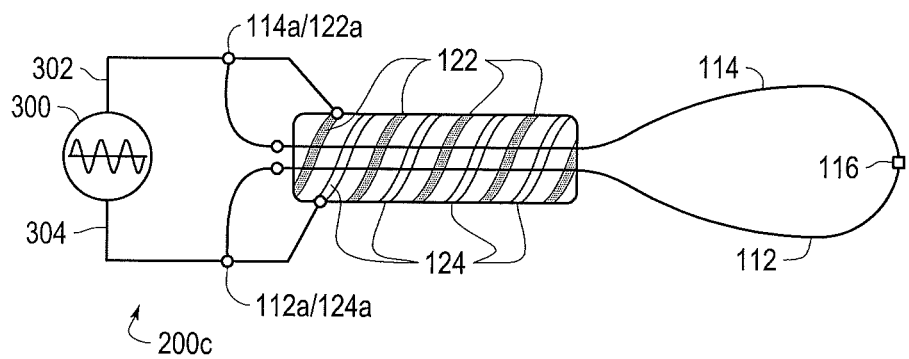
FIG. 5 is a diagram of circuitry by which the snare electrodes and the surface electrodes are concurrently activated.

As shown in FIGS. 3-5, a bipolar energy source 300 is provided and supplies energy to the snare and surface electrodes 112, 114, 122, 124 via circuitry 200a, 200b or 200c. According to the embodiments shown in FIGS. 3 and 4, energy is selectively supplied to either the snare electrodes or to the surface electrodes such that cutting by the snare electrodes occurs prior to coagulation by the surface electrodes. In the embodiment shown in FIG. 5, energy is simultaneously supplied to both the snare electrodes and to the surface electrodes such that cutting by the snare electrodes occurs concurrently with coagulation by the surface electrodes. The FIG. 5 embodiment thus is very effective at minimizing bleeding and reducing procedure time.

As shown in FIGS. 3-5, the alternating outputs of the bipolar energy source 300 (also referred to as the positive and negative outputs) are coupled to first terminal 302 and second terminal 304 respectively. As noted above, circuitry (200a, 200b or 200c) couples the first and second terminals 302, 304 to the bipolar surface electrodes 122, 124 and to the first and second snare electrodes 112, 114. Such circuitry is used to control the supply of bipolar energy to the surface electrodes and to the snare electrodes. The circuitry couples the first and second terminals 302, 304 to conductors associated with proximal ends of the bipolar surface electrodes and of the first and second snare electrodes; however, for purposes of simplicity of explanation, the conductors also are considered to be part of the proximal ends of the electrodes. Thus, snare electrode 112 has proximal end 112a, snare electrode 114 has proximal end 114a, surface electrode 122 has proximal end 122a, and surface electrode 124 has proximal end 124a.

According to the embodiments shown in FIGS. 3 and 4, the circuitry (200a or 200b) selectively causes either the snare electrodes 112, 114 or the surface electrodes 122, 124 to become "active." In such embodiments, the circuitry includes a switching device (250 or 260) by which the first and second terminals 302, 304 are selectively coupled to either (i) the proximal ends 122a, 124a of the bipolar surface electrodes 122, 124, or (ii) the proximal ends 112a, 114a of the first and second snare electrodes 112, 114. According to the FIG. 3 embodiment, the switching device 250 includes (a) a first relay 252 that selectively couples the first terminal 302 to either the proximal end 122a of the bipolar surface electrode 122 or to the proximal end 114a of the snare electrode 114, and (b) a second relay 254 that selectively couples the second terminal 304 to either the proximal end 124a of the bipolar surface electrode 124 or to the proximal end 112a of the snare electrode 112.

According to the FIG. 3 embodiment, when in a first state, the first relay 252 couples the first terminal 302 to the proximal end 114a of a first one of the snare electrodes 114 while the second relay 254 couples the second terminal 304 to the proximal end 112a of a second one of the snare electrodes 112. In addition, when in a second state, the first relay 252 couples the first terminal 302 to the proximal end 122a of a first one of the bipolar surface electrodes 122 while the second relay 254 couples the second terminal 304 to the proximal end 124a of a second one of the bipolar surface electrodes 124. The two relays 252 and 254 also can be considered to be a two pole relay.

According to the FIG. 4 embodiment, the first terminal 302 is coupled to both the proximal end 122a of a first one of the bipolar surface electrodes 122 and to the proximal end 114a of the first snare electrode 114, and the switching device includes a relay 260 that selectively couples the second terminal 304 to either the proximal end 124a of a second one of the bipolar surface electrodes 124 or to the proximal end 112a of the second snare electrode 112. In the FIG. 4 embodiment, when in a first state, the relay 260 couples the second terminal 304 to the proximal end 112a of the second snare electrode 112, and when in a second state, the relay 260 couples the second terminal 304 to the proximal end 124a of the second bipolar surface electrode 124.

According to the FIG. 5 embodiment, circuitry 200c causes both the snare electrodes 112, 114 and the surface electrodes 122, 124 to be "active" at the same time. In particular, the circuitry 200c simultaneously couples (a) the first terminal 302 to the proximal end 122a of a first one of the bipolar surface electrodes 122 and to the proximal end 114a of the first snare electrode 114, and (b) the second terminal 304 to the proximal end 124a of a second one of the bipolar surface electrodes 124 and to the proximal end 112a of the second snare electrode 112. Accordingly, the bipolar surface electrodes 122, 124 and the bipolar snare electrodes 112, 114 are concurrently supplied with power so that coagulation can be promoted as the fibroid (or polyp) is excised by the snare electrodes. This further reduces bleeding and shortens the overall procedure. The energy source 300 is simply switched on or off to control the supply of power to all of the electrodes 112, 114, 122, 124.

The electrical circuits are shown schematically in FIGS. 3-5, and can be implemented many different ways, and also may vary depending on the type of generator to which the device is connected. For example, if the generator has multiple output lines for (bipolar) coagulation and cut, the electrosurgical device could be connected to more than one of the lines (for example, a first line or port that provides bipolar coagulation energy and a second line or port that provides bipolar cutting energy), and the switching could be performed depending on which of the ports was selected to be activated by the user. In such an implementation, the user could, for example, select between different switches or buttons provided on the generator. Alternatively, switches could be provided on the device itself (e.g., on the handpiece of the device) in order to switch between which electrodes (snare electrodes and/or surface electrodes) are to receive energy, and then the energy would be supplied when an activation button/switch is pressed. Furthermore, a capacitance could be included in the circuitry such that different levels of energy are provided to the snare electrodes versus the surface electrodes based on a single output of the generator such that the snare electrodes are supplied with an appropriate cutting energy, whereas the surface electrodes are supplied with an appropriate coagulation energy.

The illustrated exemplary embodiments are intended to be illustrative and not limiting. Various changes may be made without departing from the spirit and scope of the invention.

What is claimed is:

1. An electrosurgical device comprising:
   a probe having a proximal end and a distal end;
   bipolar surface electrodes adjacent the distal end of the probe, the bipolar surface electrodes being separated from each other by a gap and extending over the distal end of the probe;
   a bipolar snare extending distally from the distal end of the probe and including first and second snare electrodes, the bipolar snare including a handpiece coupled to a proximal end of at least one of the snare electrodes, the handpiece being configured to be manipulated by a user to tighten the bipolar snare around a part of a stem of a pedunculated tissue structure to be removed;

first and second terminals by which the electrosurgical device is coupled to a bipolar energy source; and circuitry coupling the first and second terminals to the bipolar surface electrodes and to the first and second snare electrodes, the circuitry coupling the first and second terminals to proximal ends of the bipolar surface electrodes and to proximal ends of the first and second snare electrodes, the circuitry including a first relay by which the first terminal is selectively coupled to either (i) the proximal end of a first one of the bipolar surface electrodes, or (ii) the proximal end of the first snare electrode.

2. The electrosurgical device according to claim 1, wherein the bipolar snare includes an electrically insulative member disposed between distal ends of the first and second snare electrodes.

3. The electrosurgical device according to claim 2, wherein an insulative material is disposed between the bipolar surface electrodes.

4. The electrosurgical device according to claim 1, wherein an insulative material is disposed between the bipolar surface electrodes.

5. The electrosurgical device according to claim 1, wherein the bipolar surface electrodes include a first surface electrode and a second surface electrode separated from the first surface electrode by the gap.

6. The electrosurgical device according to claim 5, wherein the first and second surface electrodes each are strips of electrically conductive material and are arranged so as to alternate with each other over the distal end of the probe.

7. The electrosurgical device according to claim 5, wherein the first and second surface electrodes are formed into a double helix around the distal end of the probe.

8. The electrosurgical device according to claim 1, wherein the circuitry further comprises
   a second relay that selectively couples the second terminal to the proximal end of either a second one of the bipolar surface electrodes or the second snare electrode.

9. The electrosurgical device according to claim 8, wherein
   the first relay couples the first terminal to the proximal end of the first one of the bipolar surface electrodes while the second relay couples the second terminal to the proximal end of the second one of the bipolar surface electrodes, and
   the first relay couples the first terminal to the proximal end of the first snare electrode while the second relay couples the second terminal to the proximal end of the second snare electrode.

10. The electrosurgical device according to claim 1, wherein
   the second terminal is coupled to the proximal end of a second one of the bipolar surface electrodes and to the proximal end of the second snare electrode.

* * * * *